(12) United States Patent
Schermer

(10) Patent No.: US 7,271,885 B2
(45) Date of Patent: Sep. 18, 2007

(54) PLASMON RESONANCE MEASURING METHOD AND APPARATUS

(75) Inventor: Mack Schermer, Belmont, MA (US)

(73) Assignee: Perkinelmer LAS, Inc., Boston, MA (US)

( * ) Notice: Subject to any disclaimer, the term of this patent is extended or adjusted under 35 U.S.C. 154(b) by 281 days.

(21) Appl. No.: 11/090,583

(22) Filed: Mar. 25, 2005

(65) Prior Publication Data

US 2005/0213101 A1    Sep. 29, 2005

Related U.S. Application Data

(60) Provisional application No. 60/521,280, filed on Mar. 25, 2004.

(51) Int. Cl.
G01N 21/41    (2006.01)

(52) U.S. Cl. ..................................... 356/134

(58) Field of Classification Search ......... 356/128–137
See application file for complete search history.

(56) References Cited

U.S. PATENT DOCUMENTS

| | | | |
|---|---|---|---|
| 4,451,147 A * | 5/1984 | Dobes et al. ............... | 356/135 |
| 4,640,616 A | 2/1987 | Michalik | |
| 4,815,843 A | 3/1989 | Tiefenthaler et al. | |
| 4,844,613 A | 7/1989 | Batchelder et al. | |
| 4,889,427 A * | 12/1989 | Van Veen et al. ........... | 356/445 |
| 4,997,278 A | 3/1991 | Finlan et al. | |
| 5,341,215 A * | 8/1994 | Seher ......................... | 356/445 |
| 5,351,127 A * | 9/1994 | King et al. .................. | 356/445 |
| 5,623,561 A | 4/1997 | Hartman | |
| 5,633,724 A * | 5/1997 | King et al. .................. | 356/445 |
| 5,738,825 A * | 4/1998 | Rudigier et al. ......... | 422/82.11 |
| 5,791,691 A | 8/1998 | Charles, Jr. | |
| 5,926,284 A * | 7/1999 | Naya et al. .................. | 356/445 |
| 5,991,488 A * | 11/1999 | Salamon et al. ............ | 385/129 |
| 6,239,876 B1 | 5/2001 | Brandenberg | |
| 6,335,793 B1 | 1/2002 | Freeman et al. | |
| 6,396,576 B1 | 5/2002 | Bleyle | |
| 6,462,809 B1 | 10/2002 | Ryan et al. | |
| 6,594,011 B1 * | 7/2003 | Kempen ..................... | 356/369 |
| 6,791,691 B2 * | 9/2004 | Ohtsuka et al. ............. | 356/445 |
| 6,801,317 B2 | 10/2004 | Hofmann | |

(Continued)

FOREIGN PATENT DOCUMENTS

JP    10109082    11/1999

(Continued)

Primary Examiner—Roy M. Punnoose
(74) Attorney, Agent, or Firm—Cesari & McKenna, LLP

(57) ABSTRACT

Detection apparatus for performing surface plasmon resonance (SPR) measurements on a sample includes a support having side walls and a bottom wall defining a plurality of adjacent wells. The bottom wall has integrated therein SPR detectors underlying the wells for detecting the refractive indexes of samples deposited in the wells. Each SPR detector includes a prism having an exterior entrance surface, an exterior exit facet and an interior sensing surface located at the bottom of the overlying well, and a thin metal layer coated on the sensing surface. The prism may be molded from a transparent polymer into the bottom of a standard-format microplate structure. That structure may be used in conjunction with an SPR measuring or reading instrument to perform label-less assay measurements on various samples in an efficient and reliable manner. A method of acquiring the assay measurements is also disclosed.

24 Claims, 4 Drawing Sheets

U.S. PATENT DOCUMENTS

| | | |
|---|---|---|
| 6,864,984 B2 | 3/2005 | Naya et al. |
| 6,885,454 B2 * | 4/2005 | Naya et al. ............. 356/445 |
| 7,030,988 B2 * | 4/2006 | Kubo et al. ............. 356/445 |
| 2003/0026891 A1 | 2/2003 | Qiu et al. |
| 2003/0112427 A1 | 6/2003 | Ryan et al. |

FOREIGN PATENT DOCUMENTS

| | | |
|---|---|---|
| JP | 11304693 A * | 11/1999 |
| WO | WO98/46981 | 4/1998 |
| WO | WO 01/86262 A1 | 5/2001 |

* cited by examiner

PLASMON RESONANCE MEASURING METHOD AND APPARATUS

CROSS-REFERENCE TO RELATED APPLICATION

The present application claims the benefit of Provisional Application Ser. No. 60/521280, filed Mar. 25, 2004, the contents of which are hereby incorporated herein by reference.

BACKGROUND OF THE INVENTION

The present invention relates to surface plasmon resonance detection and measurement. It relates especially to the application of this technique to perform biological assay measurements reliably on a high volume basis.

1. Field of the Invention

Surface plasmon resonance (SPR) is an established technique for sensing and measuring refractive index changes in materials and especially for the label-less detection of biological and biochemical assays. Surface plasmon resonance biosensors use surface plasma waves to probe biomolecular interactions occurring at the surface of a sensor; see e.g. U.S. Pat. No. 4,844,613 (Batchelder et al.) and 4,997,271 (Finlen et al.).

Measuring instruments incorporating SPR detectors having a variety of optical geometries have been used to obtain SPR signals. One widely used configuration known from the former patent above is shown diagrammatically in FIG. 1. There, a light source 2 directs diverging monochromatic light rays 3, i.e. the interrogation beam, spanning a range of angles at the entrance surface 4a of a high index triangular glass prism 4. The rays are refracted upon passing into the prism where they impinge upon a prism surface 4b, i.e. a sensing surface, coated with a thin layer 5 of metal, e.g. gold. The fan of rays is reflected from that surface and exits the prism 4 from an exit surface 4c. The reflected light rays 6 impinges upon an imaging detector array 7 that produces an output signal which, when processed properly, may control a display device to produce an image 8.

As seen from FIG. 1, the image 8 has a substantially uniform intensity except at a small band or feature 8a projecting the angle attenuated by the SPR effect where the image is significantly less bright. An example of a reflection verses angle function of the image 8 produced by the FIG. 1 instrument as illustrated in FIG. 2. In angular space, the relatively dark attenuation band or feature 8a is typically less than 1° wide and the instrument detects and measures the location of that feature. The angle at which maximum attenuation of a particular wavelength of the incident light occurs is dependent upon the index of refraction of a layer 9 of a material deposited on top of metal layer 5. Thus the movement of the dark feature 8a in the overall image 8 reflects refractive index changes in the material layer 9 on the metal layer 5.

While the SPR detector illustrated in FIG. 1 has the metal coating 5 applied directly to the prism, most detectors of this type used to perform assays, e.g. for biological screening, have the metal layer on a separate flat optical element or plate which is optically coupled to the prism. Also other prism shapes are possible.

FIG. 3 shows a SPR detector known from the latter patent above, wherein the metal layer 10 is deposited on a flat glass plate 12 which forms the bottom wall of a flow cell 14 defining a cavity 14a containing a sample 16 which contacts the metal layer 10 within the cavity. The flow cell 14 including the coated plate 12 may constitute a disposable unit 17 which is removably coupled by an index matching liquid 18 such as oil, to the flat surface 20a of a glass prism 20, in this example a hemispherical or semicylindrical prism, which is usually a fixed part of the measuring instrument. Interrogating light rays 22, in this case a converging beam, enter one side of prism 20 and are brought to a focus at a point P located at the metallized surface of plate 12 near the center of curvature of prism 20. Light which is internally reflected at point P passes out through the opposite side of the prism as measuring rays 24 which impinge on a detector array 26. As in the FIG. 1 instrument, detector 26 produces an image having a dark feature whose position in the image reflects the index of refraction of sample 16 in the flow cell 14.

SPR assay implementations using flow cells such as the one in FIG. 3 have a relatively low throughput because it takes time to pump enough of a particular sample into the flow cell cavity to clear material from a previous measurement in that same cell and to stabilize a new concentration of material for the new measurement. Also as noted above, index matching liquid 18 must be present between the flow cell unit 17 and the surface 20a of prism 20. This fluid must be applied consistently with no bubbles before coupling the flow cell unit to the prism. Moreover, flow cell unit separation from the prism after measurement is difficult because of the need to overcome surface tension between the opposing surfaces of the unit 17 and the prism. Still further, the liquid 18 must be cleaned from the prism and from the flow cell unit after each assay to avoid the buildup of contaminants which could degrade the next measurement using that same unit. Such required maintenance steps slow down the SPR measurements and reduce the throughput of the measuring instrument as a whole.

Because of the inconvenience of having to repeatedly couple and decouple the flow cell unit to the fixed prism using the index matching liquid and also because of the expense of the flow cell unit per se, these units are often reused for multiple assays or tests. Researchers have validated processes that accommodate such reuse. However, concerns about potential cross-contamination between samples have to be addressed following complex disassociation and washing protocols which are time consuming and reduce the throughput of the measuring instrument as a whole. Moreover, such re-use of the flow cell units bucks the overall trend towards the use of disposable labwear in life science research.

In biological screening, large numbers of assays have to be performed in parallel. Likewise in many life science research or drug discovery settings, multiple samples need to be measured in a single session. For these reasons, molded microplates defining a multiplicity of sample wells are very commonly used in these fields for performing assays with signal-producing label chemistries such as fluorescence, luminescence or radioactivity. Microplates having 96, 384 and 1586 wells are made to standardized dimensions prescribed by the Society for Biomolecular Screening (SBS). Considerable instrumentation, automation and infrastructure have been developed over the years at life science research and drug discovery institutions to accommodate assays using these microplates. However, until now no one has thought to incorporate SPR detection features into a microplate-type structure because of the seemingly insurmountable obstacle to interrogating and measuring samples in the densely packed wells of the microplate.

Therefore, it would be desirable if there existed SPR detection and measuring apparatus that combines the simplicity and low cost of a fixed-prism measuring instrument with the throughput and ease of handling of a standard-format microplate.

SUMMARY OF THE INVENTION

Accordingly, the present invention aims to provide SPR detection apparatus which may be embodied in a standard format microplate of the type commonly used to perform assays so that it can be manipulated by equipment normally used to handle conventional microplates.

A further object of the invention is to provide such apparatus which is relatively easy and inexpensive to manufacture in quantity.

Still another object of the invention is to provide SPR detection apparatus of this type which, when coupled to a SPR reading instrument, enables the quick and reliable reading of multiple samples in a minimum amount of time.

Yet another object of the invention is to provide SPR detection and measuring apparatus which can reliably perform biological assay measurements on a high volume basis.

Another object of the invention is to provide SPR detecting and measuring apparatus which can detect the refractive indexes and index changes of multiple samples over time.

A further object of the invention is to provide a method of performing assay measurements utilizing SPR detection apparatus of this type.

Other objects will, in part, be obvious and will, in part, appear hereinafter.

The invention accordingly comprises several steps and the relation of one or more of such steps with respect to each of the others, and the apparatus embodying the features of construction, combination of elements and arrangement of parts which are adapted to effect such steps, all as exemplified in the following detailed description, and the scope of the invention will be indicated in the claims.

Briefly, the present apparatus comprises a support defining a plurality of wells, preferably arranged in a rectangular array having a standard microarray format. These wells are adapted to contain samples, e.g. for performing an assay. Integrated into the bottoms of the wells are SPR detectors consisting of depending optical prisms, with each prism having exterior entrance and surface facets and an interior metallized sensing surface at the bottom of the overlying well. Preferably, each prism is in the form of an inverted irregular trapezoid with the base of the trapezoid constituting the sensing surface and the sides of the trapezoid constituting the entrance and exist surfaces. The prism exterior surface opposite the base is preferably angled downward toward the exit surface for reasons to be described in detail later.

The support member is adapted to be used in conjunction with an assay measuring or reading instrument comprising a light source for emitting an interrogating beam of linearly polarized, preferably monochromatic, light, a detector for detecting that light and a moveable fixture for removably holding the support. The instrument also includes an addressable x-y positioning mechanism for moving the fixture and the source/detector pair relatively so that the interrogating beam can be directed to the entrance surface of the prism under any well in the support.

In use, the interrogating beam is refracted upon entering the selected prism and propagated to the sensing surface of that prism where it is reflected. The reflected light leaves the prism via the exit surface thereof whence it is directed to the instrument's detector as an SPR measuring beam. The detector, upon receiving the measuring beam, produces a signal which reflects the index of refraction of the sample resident in the well being interrogated by the instrument. In other words, the interrogation rays are reflected from the metallized sensing surface except at the SPR attenuation band, whose location in the image depends upon the index of refraction of the sample in the well being interrogated.

As will be seen, the geometry of the support member with its integrated SPR detectors and the measuring instrument optics are designed and correlated so that the SPR detectors in the support do not interfere with the relative movement of the support and instrument optics and do not occlude the light beams when the instrument is interrogating adjacent wells.

Also as will be described later, the present invention enables the performing of assays utilizing variously sized standard format microplate structures incorporating the SPR detectors. Using these structures, specific binding assays may be performed when one member of a specific binding pair is immobilized at the bottom of each well of the microplate structure and assay measurements may be acquired at different times to provide an indication of assay kinetics.

BRIEF DESCRIPTION OF THE DRAWINGS

For a fuller understanding of the nature and objects of the invention, reference should be made to the following detailed description taken in connection with the accompanying drawings, in which FIG. 1, already described, is a diagrammatic view of a prior measuring instrument comprising a SPR detector whose metal sensing layer is applied directly to the detector's prism.

DETAILED DESCRIPTION OF AN ILLUSTRATIVE EMBODIMENT

Figure 4:
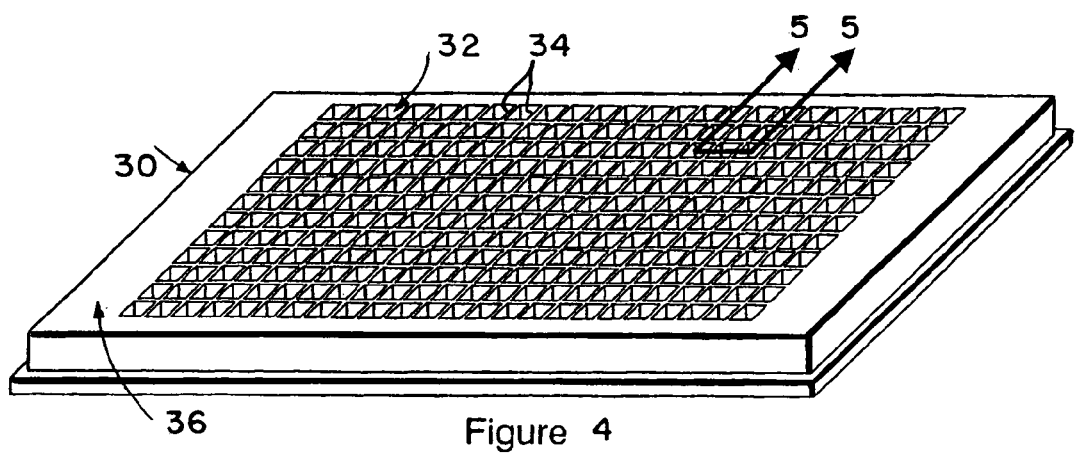
FIG. 4 is an isometric view of SPR detection apparatus based on the SBS microplate standards and incorporating the invention.
Figure 5:
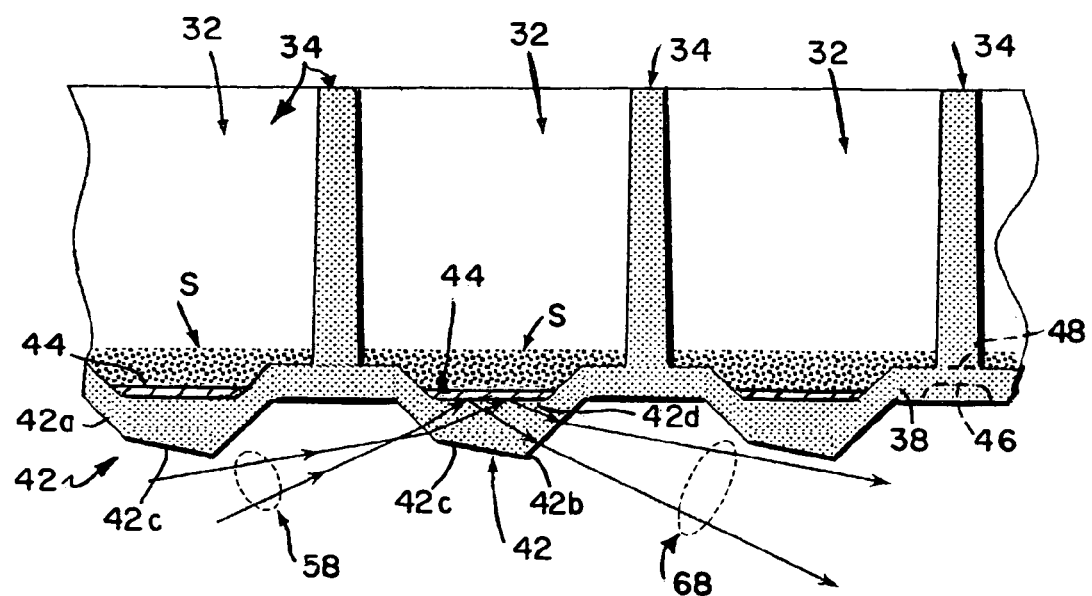
FIG. 5 is a fragmentary sectional view on a much larger scale taken along line 5-5 of FIG. 4.

Referring now to FIGS. 4 and 5 of the drawings, in accordance with the present invention, my SPR detection apparatus comprises a support 30 preferably implemented as a standard-format microplate structure as shown in FIG. 4, which structure may be considered a disposable item. Support 30 defines a rectangular array of wells 32 arranged in columns and rows, with the adjacent wells being separated by walls 34. The well array is surrounded by a skirt 36 to support the wells. The illustrated support 30 corresponds to a microplate with 384 wells. The wells are spaced on 4.5 mm centers and their walls are 1 mm thick. Plates with 24, 96 and 1536 are also commonly used in life science research and the drug industry. It should be understood, however, that aspects of the present invention are applicable to a support with only a few or even a single well 32. In any event, the walls 34 extend up from a plate bottom wall 38 allowing each well to receive and support an assay reagent or sample S whose refractive index may be measured as will be described later.

As best seen in FIG. 5, a prism shown generally at 42 is integrated right into the bottom wall 38 under each well 32. In the illustrated support 30, each prism 32, in cross-section, is an inverted irregular trapezoid which extends down below each well 32. One exterior side wall of the prism constitutes an entrance surface 42a preferably in the form of a facet, the opposite side wall constitutes an exit surface or facet 42b, and a third exterior surface or facet 42c, which is inclined, extends between the lower edges of the facets 42a and 42b. Preferably, facets 42a and 42b extend down at an angle of about 45°, but facet 42b is deeper than facet 42a so that facet 42c is inclined at an angle of about 10° relative to bottom wall 38.

Still referring to FIG. 5, each prism 42 also includes a flat horizontal interior base surface or facet 42d at the bottom of the associated well 32. This facet which constitutes a sensing surface, is located opposite facet 42c but also overlies portions of facets 42a and 42b. Surface 42d is coated with a thin, e.g. 50 nm, layer 44 of a metal such as gold, typically by vacuum sputtering. Thus, a metal-coated prism, constituting an SPR detector is located at each well 32 of the support 30.

Support 30 or at least the prisms 42 thereof is preferably molded of a transparent polymer such as polystyrene, polycarbonate, polysulfone and polymethylmethacrylate (PMMA). The geometry of the prisms 42 has been designed in a manner consistent with high quality results from the injection molding process normally used to form microplates. As noted above, the prisms are integrated with the bottom wall 38 of the support, which is, in turn, integrated with the well separation walls 34.

Indeed the geometries of the prisms 42 and the support structure shown in FIG. 5 illustrate the suitability of the structure of the invention for the injection molding processes. More particularly, the walls 34 between the wells are shown with a 1° draft angle to facilitate ejection of the plate from that side of a mold. The bottom or prism side of the plate exhibits relatively large angle drafts allowing a mold to be pulled directly away from the prism facets 42a and 42b thereby assuring optical surfaces of high quality. The prisms themselves fulfill their optical functions to be described while restricting their maximum thickness to about 1.5 times that of the nominal plate structure which may have a thickness dimension between, say, 1 and 2 mm. This facilitates cooling of the structure in the mold with minimal warping particularly in view of the relatively high surface area-to-mass of the support 30.

Still further, due to polymer cooling and shrinking at the junctions of the plate walls 34 with the plate bottom wall 38, sinks may form in wall 38 as indicated in phantom at 46 in FIG. 5. However, as seen there, the sinks are remote from the locations of prisms 42 and thus do not affect the optical properties of the prisms. Resultantly, the overall plate geometry combines the ease of microplate manufacture while optimizing the optical quality of the prisms 42.

It is important to appreciate that the support 30 may be molded such that a discrete prism 42 exists under each well 32 or such that a single long prism 42 extends under all of the wells 32 in a given row (or column) of the microplate. In other words, the prisms 42 in FIG. 5 may extend the full width of the well array shown in FIG. 4. This multi-well prism structure has the advantage of a simpler mold design and fabrication process and produces a more mechanically rigid molded part. On the other hand, separate, discrete prisms 42 with gaps between them have a higher surface area-to-mass ratio and thus may solidify in a mold with less distortion.

Also instead of forming support 30 as a unitary part, the bottom wall 38 including prisms 42 may be molded as a separate part from walls 34 and skirt 36 which can be formed according to SBS standards as a bottomless microplate part. Those parts may then be bonded together as indicated at 48 at the base of the right hand transverse wall 34 in FIG. 5. This enables the optically critical parts of the apparatus to be formed using a higher quality material and/or molding process then are/is used for the less important parts of the microplate. For example, for some applications it may be desirable to form the bottom wall 38 with a prism 42 of high quality glass or other material that is transparent to the desired interrogation wave-length from a light source. That glass structure may then be secured to a bottomless upper plate structure of plastic that conforms to the SBS standards.

Figure 6:
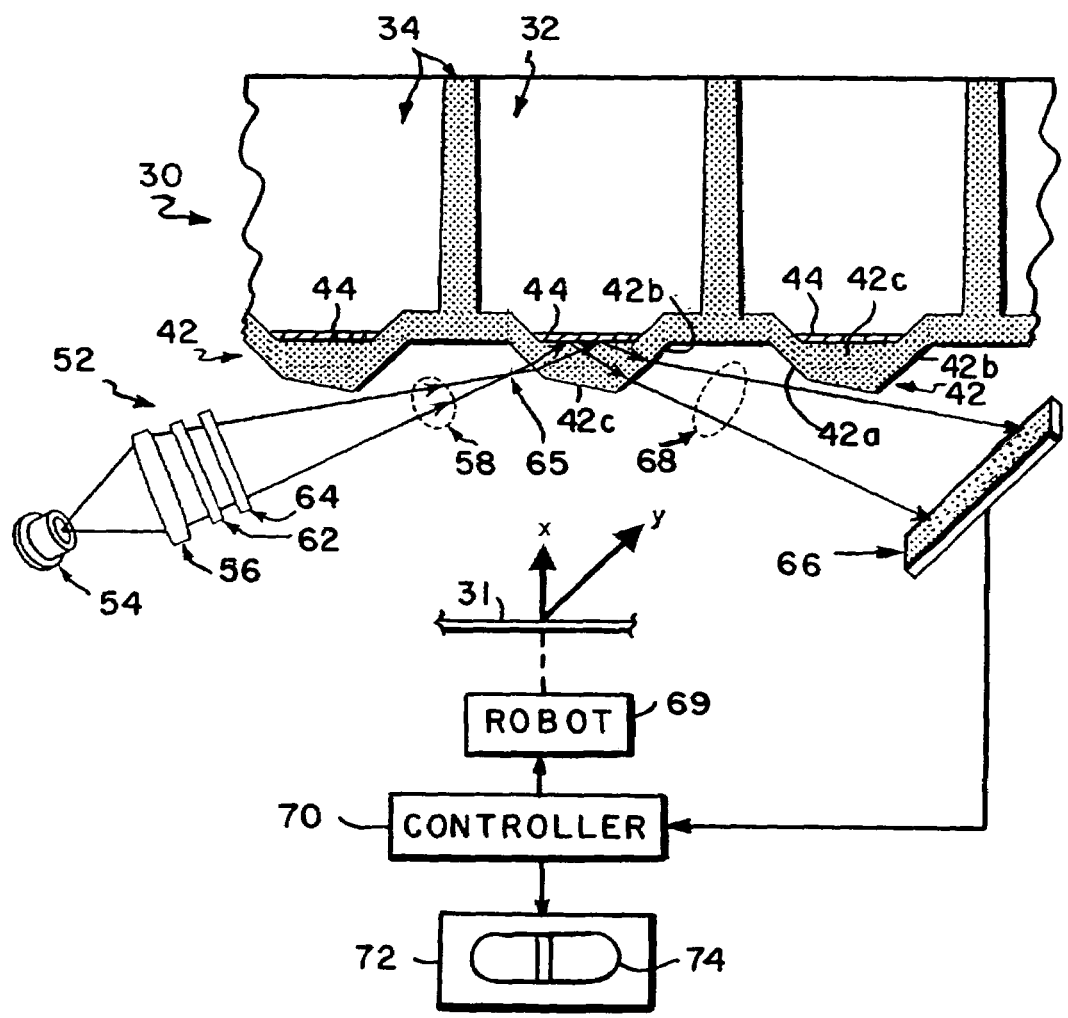
FIG. 6 is a diagrammatic view showing the FIG. 4 apparatus as part of a SPR measuring or reading instrument.

Refer now to FIG. 6 which illustrates an assay measuring or reading instrument shown generally at 52 for use in association with support 30 to acquire assay measurements of samples S in the wells 32 of the support. The instrument includes a light source 54 which may be a light emitting diode (LED), superluminescent diode (SLD) or a simple light bulb. A preferred light source is either a diode laser or a LED both of which have high brightness and high electrical efficiency. The light source may emit light at various wavelengths usually ranging from the visible to the near infrared (500-900 nm). The light from light source 54 is preferably focused by beam-shaping optics 56 to produce interrogation rays 58 which are incident on the entrance facet 42a of the prism 42 under a selected plate well 32. If the light from light source 54 is not monochromatic, wavelength filtering optics 62 may be positioned after optics 56 to produce monochromatic interrogation rays. Also polarization optics 64 may be incorporated into the interrogation path depending upon the inherent polarization properties of the light source 54. This is because the interrogation rays should be linearly polarized to produce the SPR effect.

Figure 3:
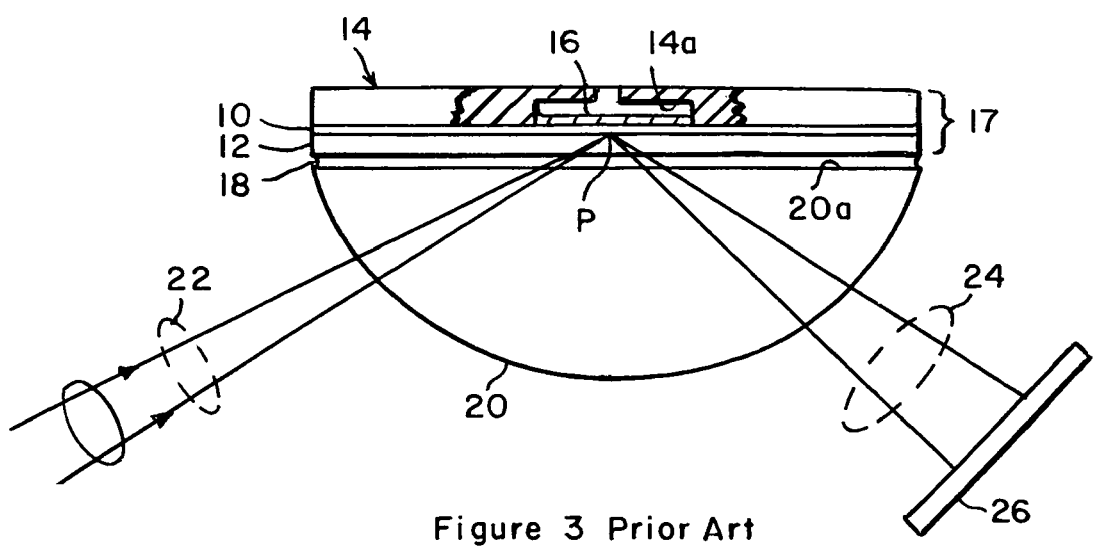
FIG. 3, already described, is a diagrammatic view of another prior SPR measuring instrument comprising a SPR detector which is part of a flow cell whose metal sensing layer is applied to a flat plate removably optically coupled to the prism.
Figure 2:
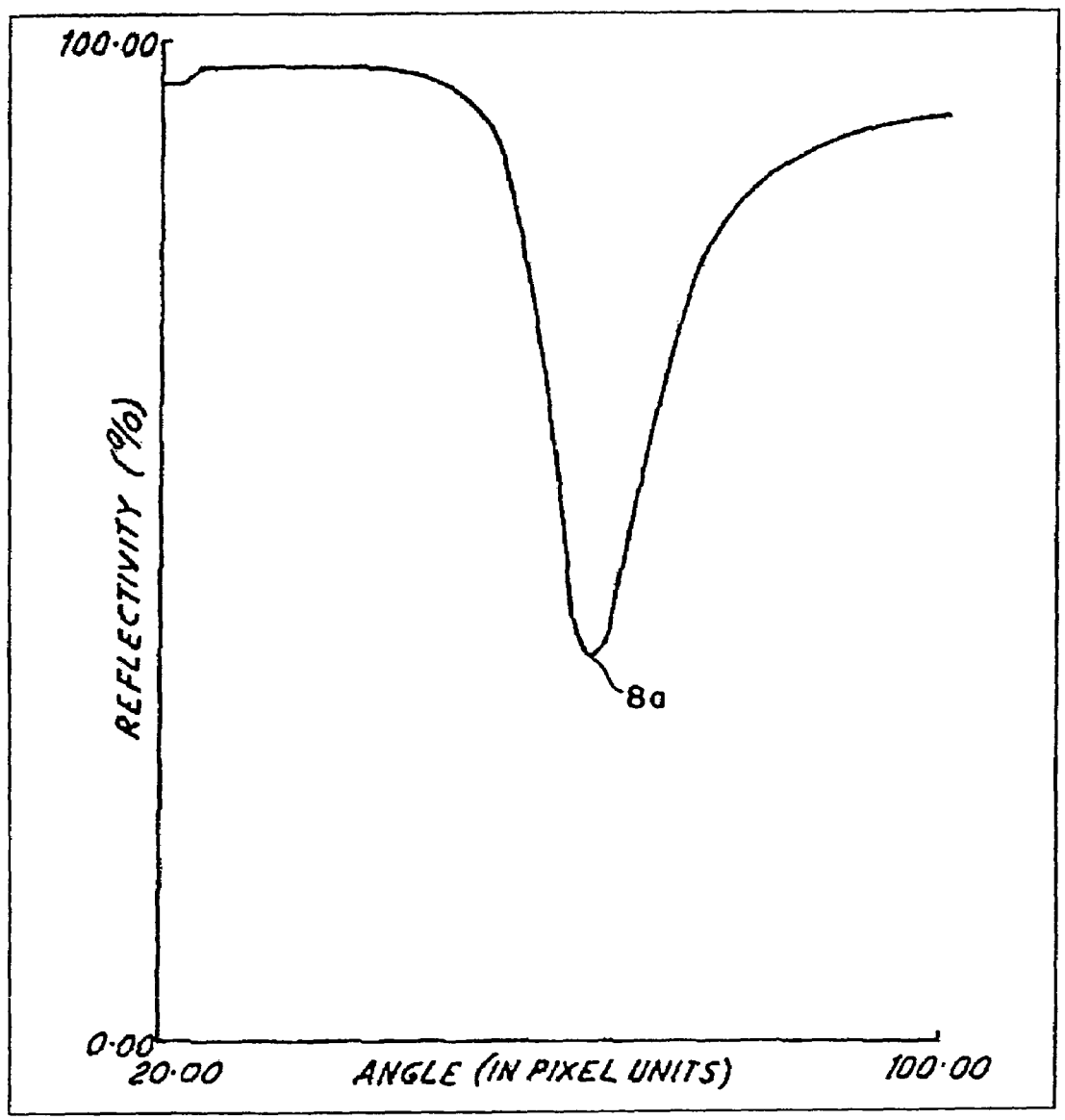
FIG. 2, already described, is a graph showing the measured SPR response function of the FIG. 1 instrument.

In any event, the light source and related optics must produce an interrogation beam with the range of angles required to obtain the geometry of SPR excitation at the selected prism 42. The beam shape may be converging, diverging or collimated. Preferably, however, as shown in FIG. 6, the beam should converge to a focus at a point 65 just ahead of prism facet 42a. This focus constitutes a virtual point source from which a fan of diverging interrogation rays can be viewed to originate. This arrangement is advantageous over a diverging lens system such as shown in FIG. 3 in that it allows the light source 54 and beam forming optics to be spaced away from the bottom of the microplate. Thus, the microplate is free to move relative to the fixed components of instrument 52 thereby assuring that the instrument can interrogate any well 32 in the microplate without obstructing the light paths between the light source and detector array. Collimated beam forming optics for SPR imaging can, of course, be placed far away from the bottom of the support 30.

The beam shaping optics 56 may be a conventional spherical lens, but is preferably a cylindrical lens or other anamorphic lens when using a converging/diverging beam arrangement. A cylindrical lens creates a line focus at point 65 so that the interrogation rays 58 have the converging/diverging angles shown in the plane of FIG. 6, but are substantially collimated or parallel in the plane perpendicular to that figure. Thus, in this arrangement, the SPR measurement may be taken on a line across the entire surface of the metal layer 44 at the bottom of a well 32 rather than on just a small point-like area. This reduces sensitivity to point defects anywhere in the optical path from light source 54 and helps to average out any inhomogeneities in the assay on the measuring surface 42d of well 32.

Still referring to FIG. 6, instrument 52 also includes an imaging detector 66 positioned to receive the measuring light rays 68 emanating from the exit facet 42b of prism 42. The detector may be a one or two-dimensional CCD imaging array, a CMOS imaging array, a photodiode array or other known array used for these purposes. Alternatively, the detector 66 may be a single element sensor such as a photodiode or a photomultiplier tube. With a single element sensor, the integrated optical power goes up or down as more or fewer TIR waves are incident on the detector as dictated by the refractive index of the sample S being measured. Preferably, the measuring rays 68 are angled downward as shown so that the detector 66 can be placed far enough away from the bottom wall 38 of the microplate so that the top of the detector clears prisms 42 when the microplate 30 moves relative to the detector as instrument 52 interrogates the various wells 32.

The support 30 may be positioned in a fixture 31 moveable in the x and y directions by a positioning mechanism or robot 69 under the control of a controller 70. The controller can be programmed to move support 30 so that instrument 52 can interrogate and take measurements at the SPR detector under any well 32 in the microplate such as the one centered in FIG. 6.

The measuring rays 68 reflected at the sensing surface 42d from the selected prism 42 are detected by the detector 66 which thereupon produces an output signal. That signal is applied to known analysis software in controller 70 which may control an output device 72 which thereupon displays or indicates the index of refraction of the sample S in the well 32 being interrogated as illustrated by the image 74 in FIG. 6.

The measuring instrument 52 according to the invention may have one light source/detector pair and measure one well 32 at a time. More preferably, the instrument includes a plurality of source/detector pairs in parallel to increase the throughput of the instrument. For example, source/detector pairs may extend under all or part of a column of wells 32 in the microplate array shown in FIG. 4. By indexing the fixture 31 in FIG. 6 in the x direction, multiple wells in a given column may be interrogated at the same time.

Figure 1:
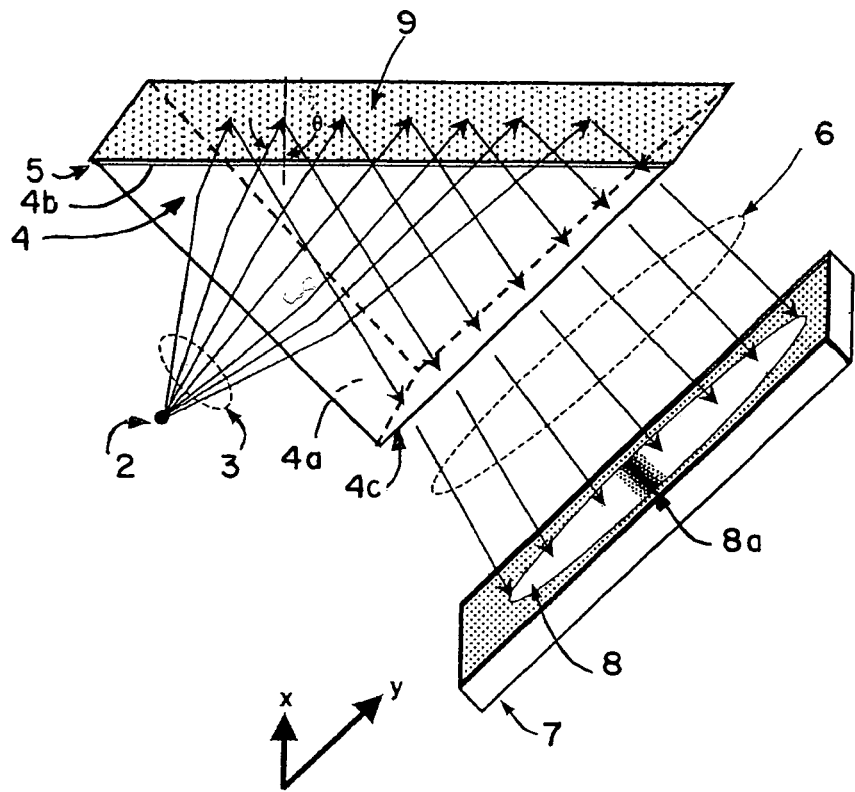

It is apparent from FIG. 6 that the providing of multiple, specially shaped SPR detectors as integral parts of a disposable microplate structure greatly facilitates the assay measuring process. As discussed at the outset, many known SPR detectors comprise triangular, high-index glass prisms such as shown in FIG. 1. While this geometry would superficially appear to be moldable in plastic, it cannot easily be combined with the closely spaced wells of a multi-well support structure such as a microplate. Moreover, the triangular prism of the prior detector would interfere with the beam paths of both the interrogation and measurement rays at adjacent wells if incorporated into a standard microplate. For the same reasons, other prior high profile SPR detectors such as the one shown in FIG. 3 do not lend themselves to integration into a multi-well support structure. The present apparatus avoids these problems by integrating the SPR detectors into the bottom of the microplate structure and giving the detector prisms their special inverted irregular trapezoid shape. As clearly seen in FIGS. 5 and 6, when a particular well 32 has been addressed and is being interrogated the converging interrogating rays 58 can clear the prism 42 of the adjacent well even though the light source 52 with its associating optics is relatively close to the underside of the support 30 as needs to be the case if the instrument is to be reasonably compact. Yet because the interrogating beam is brought to a focus ahead of the prism at point 65, a fan of interrogating rays are incident on the sensing surface 42b of the prism yielding the advantages noted above. Similarly, the measuring rays 68 leaving that prism 42 are not obstructed by the prism of the well 32 on the other side of the well being interrogated even though rays 68 are diverging as they leave the prism. This is because the lowermost surfaces or facet 42c of each prism 42 is inclined at an angle, e.g. about 10°, to provide clearance for the diverging rays so that they can reach a detector 66 that is placed reasonably close to the underside of support 30.

Using the apparatus described above, specific binding assays may be performed where one member of a specific binding pair is immobilized at the bottom of each well 32 of plate 30. Preferably, it is desirable to acquire assay measurements at two times. The first measuring point should be just before, just at, or just after a sample S is added to a well. This first point acquires a measurement that encompasses at least one of the specific optical properties of a given well, the refractive index of the buffer or media in which the assay is performed, and the index of refraction of the sample in solution. The second measurement may be taken after a defined assay incubation period. Then the first measurement is subtracted from the second measurement and the difference is representative of the result of the assay. This before-after or end point assay approach allows assay incubation to proceed without the need for monitoring assay progress in the reading or analysis section of the instrument.

One can also acquire sets of multiple assay measurements at regular time intervals during assay incubation. These time points can then be assembled into binding kinetic curves. While this procedure produces more information from the assay, it requires that the incubation (which may take many minutes or even hours) be performed while support 30 is in the measuring instrument 52, thereby limiting assay throughput.

It will thus be seen that the objects set forth above, among those made apparent from the preceding description are efficiently attained and, since certain changes may be made in carrying out the above method and in the construction set forth without departing from the scope of the invention, it is intended that all matter contained in the above description or shown in the accompanying drawings be interpreted as illustrative and not in a limiting sense.

It is also to be understood that the following claims are intended to cover all of the generic and specific features of the invention described herein.

What is claimed is:

1. Apparatus for performing surface plasmon resonance (SPR) measurements on a sample, said apparatus comprising a support having side walls and a bottom wall defining a plurality of wells, said wells being arranged in a rectangular array of columns and rows in a standard microplate format, said bottom wall having integrated therein SPR detectors underlying the wells for detecting the refractive indexes of samples deposited in the wells, each SPR detector including a truncated prism having an exterior entrance surface, an exterior exit surface and an interior sensing surface located at the bottom of the overlying well, and a thin metal layer coated on the sensing surface and wherein each prism cross-section is an inverted trapezoid whose base corresponds to said sensing surface and whose opposite sides correspond to said entrance and exit surfaces, each prism also having a lowermost surface opposite the sensing surface.

2. The apparatus defined in claim 1 wherein the prisms are molded into the bottom wall.

3. The apparatus defined in claim 2 wherein the prisms are of a transparent polymer.

4. The apparatus defined in claim 3 wherein the polymer is one of the group consisting of polycarbonate, polystyrene, polysulfone and polymethylmethacrylate.

5. The apparatus defined in claim 3 wherein the side walls and the bottom wall are molded as a unitary part.

6. The apparatus defined in claim 1 wherein the side walls and the bottom wall are formed separately and secured together by a bonding agent.

7. The apparatus defined in claim 6 wherein the side walls and the bottom wall are of different materials.

8. The apparatus defined in claim 7 wherein the bottom wall is of glass.

9. The apparatus defined in claim 1 wherein each prism is a segment of a longer prism element which extends under an entire row or column of wells in the support.

10. The apparatus defined in claim 1 wherein the bottom wall includes a separation between the prisms underlying adjacent wells.

11. The apparatus defined in claim 1 wherein the metal layer is of gold.

12. The apparatus defined in claim 1 wherein said sides descend from the base at equal angles and the lowermost surface declines toward said exit surface.

13. The apparatus defined in claim 1 and including a first member of a specific binding pair resident in at least one of said wells in contact with the metal layer therein to facilitate an assay.

14. The apparatus defined in claim 1 and including cells or cell fragments resident in at least one of said wells and immobilized against the metal layer therein to facilitate an assay.

15. Apparatus for performing surface plasmon resonance (SPR) measurements on a sample, said apparatus comprising a support having side walls and a bottom wall defining at least one well, said bottom wall having integrated therein a prism underlying said at least one well, each prism in cross-section having the shape of an inverted irregular trapezoid and whose base constitutes the bottom of the overlying well, whose opposite sides descend from the base toward one another and each prism also having a lowermost surface opposite the base which declines toward one of said sides.

16. The apparatus defined in claim 15 wherein said sides descend from the base at equal angles and the lowermost surface declines at an angle of about 10° relative to the base.

17. The apparatus defined in claim 15 and further including a thin metal layer coated on the base of each prism.

18. The apparatus defined in claim 17 wherein said support is of plastic and said metal layer is of gold.

19. Surface plasmon resonance (SPR) measuring apparatus comprising a fixture;

a support removably received in the fixture, said support having side walls and a bottom wall defining a multiplicity of wells for receiving samples, said walls being arranged in a rectangular array of columns and rows in a standard microplate format, said bottom wall also defining truncated prisms underlying said wells, each prism having an exterior entrance surface and an exterior exit surface, said entrance and exit surface descending from an interior metallized sensing surface located at the bottom of the associated well so that each prism has a cross-section in the shape of an inverted trapezoid;

a light source for directing interrogating light rays into a selected one of said prisms through the entrance surface thereof, said interrogating rays being reflected at the corresponding sensing surface and leaving the selected prism from the exit surface thereof as measuring rays;

an optical detector paired with the light source for collecting said measuring rays and producing a corresponding output signal;

a positioning mechanism for moving the fixture and the source/detector pair relatively, and a controller for controlling the positioning mechanism so that said multiplicity of wells can be interrogated in a selected order.

20. The apparatus defined in claim 19 and further including an output device responsive to the output signal for indicating the refractive index or index change of the sample in each interrogated well.

21. The apparatus defined in claim 19 wherein the light source provides interrogating rays which converge to a point near the entrance surface so that the interrogating rays are diverging as they pass into the selected prism.

22. The apparatus defined in claim 19 wherein the light source produces polarized light and includes a wavelength filter so that the interrogating rays are monochromatic.

23. The apparatus defined in claim 19 wherein said light source includes at least one from the group consisting of a laser, an LED, an SLD and a bulb.

24. The apparatus defined in claim 19, wherein said detector includes a CCD or a CMOS array.

* * * * *